US006951948B2

(12) United States Patent
Deng et al.

(10) Patent No.: US 6,951,948 B2
(45) Date of Patent: Oct. 4, 2005

(54) METHOD FOR SYNTHESIS OF SUBSTITUTED AZOLE LIBRARIES

(75) Inventors: Yijun Deng, North Wales, PA (US); Dennis Hlasta, Doylestown, PA (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/862,808

(22) Filed: May 22, 2001

(65) Prior Publication Data

US 2002/0042520 A1 Apr. 11, 2002

Related U.S. Application Data

(60) Provisional application No. 60/209,252, filed on Jun. 5, 2000.

(51) Int. Cl.[7] ............................................. C07D 233/64
(52) U.S. Cl. ............................... 548/336.1; 548/341.1; 548/341.5; 548/342.1
(58) Field of Search ..................... 548/336.1, 341.1, 548/341.5, 342.1, 331.8

(56) References Cited

FOREIGN PATENT DOCUMENTS

EP        0 816 310 A    1/1998
WO       WO 00 25768 A   5/2000

OTHER PUBLICATIONS

Aryl Ketones as Novel Replacements for the C–Terminal Amide Bond of Succinyl Hydorxamate MMP Inhibitors; George S. Sheppard, Biorganic & Medicinal Chemistry Letters, (1998) 3251–3256.
Pharmacological Study of a Series of α–Aminoacetanilides With Local Anesthetic Activity; M. Colombo, Farmacol Clinical Exp. (1987) 41–47.
(Methoxyalkyl) thiazoles: A New Series of Potent, Selective, and Orally Active 5–Lipoxygenase Inhibitors Displaying High Enantioselectivity; T. Geoffrey, J. Medical Chemistry (1991) 2176–2186.
Formulation of α–(10Methyl–2–Benzimidazolyl) Benzyl Benzoate By the Combined Action of Aromatic Aldehydes and Acyl Halides on I–Methylbenzimidazole; B.I. Khristich; literature cited 1136–1137, (1983).
The Thermal condensation of Imidazoles with Carbonyl Compounds; A.M.Roe; Smith–Kline and French Research Institute 2195–2200, (1963).
Reactions of Imidazoles with Isocyanates at Elevated Temperature, Elefthherios P.Papadopoulos; (1977) Department of Chemistry, University of New Mexico, 3925–3929.
Reactions of Azolels with Isocyanates at Elevated Temperature, Eleftherios P. Papadopoulos; Department of Chemistry, Univeristy of New Mexico, (1978) 99–104.

Organosilicon Compounds XV. Cleavage of the Silicon–Carbon Bond of 2–Trimethylsilyl–1–methylimidazole and 2–Trimethylsilyl–1–methylbenzimidazole: Frank H. Pinkerton; Department of Polymer Science, University of Southern Mississippi (1971) 67–72.
Synthesis of (Trimethylily)thiazoles and Reactions with Carbonyl Compounds, Selectively Aspects and Synthetic Utility. Alessandro Dondoni. University of Italy (1987) 1748–1761.
K. D. Janda, "Tagged versus untagged libraries: Methods for the generation and screening of combinatorial chemical libraries," *Proc. Natl. Acad. Sci. USA*, 1994, pp. 10779–10785, vol. 91.
Hoekstra W. J. et al., "Solid–Phase Synthesis via N–Terminal Attachment to the 2–Chlorotrityl Resin," *Tetrahedron Letters*, 1997, pp. 2629–2632, vol. 38, No. 15.
Moore M. et al., "Dipolar Cycloaddition Reactions on a Soluble Polymer–Supported Dipolarophile: Synthesis of Sugar–derived Triazoles," *Tetrahedron Letters*, 1998, pp. 7027–7030, vol. 39.
Yan B. et al., "Role of Fourier transform infrared spectroscopy in the rehearsal phase of combinatorial chemistry: a thin–layer chromatography equivalent for on–support monitoring of solid–phase organic synthesis," *Journal of Chromatography B*, 1999, pp. 91–102, vol. 725.

*Primary Examiner*—Joseph K. McKane
*Assistant Examiner*—Rebecca Anderson

(57) ABSTRACT

The invention relates to methods of synthesizing libraries of diverse and complex 2-substituted azole compounds of the general formula (I) or (II)

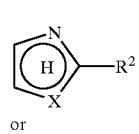

(I)

or

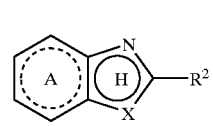

(II)

wherein X, R[2] and the ring components

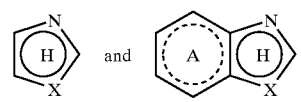

are as described herein, novel intermediates useful for synthesizing such substituted azole compounds and methods for identifying and isolating the compounds.

5 Claims, No Drawings

METHOD FOR SYNTHESIS OF SUBSTITUTED AZOLE LIBRARIES

CROSS REFERENCE TO RELATED APPLICATION

This application claims the priority of U.S. provisional application Ser. No. 60/209,252 filed Jun. 5, 2000, the contents of which are hereby incorporated by reference.

FIELD OF THE INVENTION

The present invention is directed to a method of synthesizing libraries of diverse and complex 2-substituted azole derivatives and novel intermediate compounds.

BACKGROUND OF THE INVENTION

Compounds having biological activity can be identified by screening diverse collections of compounds (i.e., libraries of compounds) produced through synthetic chemical techniques.

The generation of chemical libraries on and off solid resins have proven to be a valuable resource for the pharmaceutical industry in their endeavors to discover new drugs using high throughput screening (HTS) techniques. In creating the libraries, the compounds are ideally synthesized in situ in solution phase or on a solid support. However, relatively simple synthetic methods to produce a diverse collection of such derivatives in situ are often not available.

Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labeled receptor bound to the substrate with its location on the substrate identifies the binding compound. Using these techniques, the development of efficient high throughput screening has greatly enhanced the pharmaceutical industry's ability to screen large numbers of compounds for biological activity. Central to these methods is the screening of a multiplicity of compounds in the library and the ability to identify the structures of the compounds that have a requisite biological activity.

Pharmaceutical drug discovery relies heavily on studies of structure-activity relationships wherein the structure of "lead compounds" is typically altered to determine the effect of such alteration on activity. Alteration of the structure of the lead compounds permits evaluation of the effect of the structural alteration on activity.

Thus, libraries of compounds derived from a lead compound can be created by including derivatives of the lead compound and repeating the screening procedures. In this manner, compounds with the best biological profile, i.e., those that are most active and which have the most ideal pharmacologic and pharmacokinetic properties, can be identified from the initial lead compound.

Recently, 2-substituted oxazoles were found to be potent as MMP inhibitors (Sheppard, et al, in *Bioorg Med Chem Lett* 8(22), 3251 (1998)); 2-substituted imidazoles were found to produce local anesthetic effects (Colombo, et al., *Rev Farmacol Clin Exp*, 4(1), 41–47 (1987); and 2-substituted thiazoles were found to be selective inhibitors of 5-lipoxygenase (Bird, et al., 5th *Int Conf Inflamm Res Assoc* (Sept 23–27 Whit Haven) Abst 85, 1990).

Synthesis of substituted nitrogen containing heteroaryls using solution phase chemistry has been previously described. Khristich et al., in *Khimia Geterotsiklicheskikh Soedineii*, 8, 1136–36 (1983) describe the solution phase synthesis of α-(1-methyl-2-benzimidazolyl)benzyl benzoates. Roe et al., in *JCS* p 2195 (1963) describe the thermal condensation of imidazoles with carbonyl compounds. Papadopolous, in *J. Org. Chem.*, 42 (24) 3925–29, (1977) describes reaction of imidazoles with isocyanates, while Papadopolous et al., in *J. Org. Chem.*, 44(1) 99–104 (1979) describe reactions of azoles with isocyanates. Cleavage of the silicon-carbon bond of 2-trimethylsilyl-1-methylimidazole and 2-trimethylsilyl-1-benzimidazole to yield 2-substituted imidazoles and 2-substituted benzimidazoles is described by Pinkerton, F. H. and Thames, S. F., in *J. Heterocycl. Chem.* 9(1), 67–72 (1972). Dondoni et al., in *J. Org. Chem.*, 53, 1748–61 (1988) describe the synthesis of (trimethylsilyl)thiazoles which are reacted with carbonyl compounds to prepared highly substituted thiazoles.

In order to develop new pharmaceutical drugs to treat various disease conditions, it would be highly desirable to be able to generate such libraries of substituted azole derivatives and novel intermediate compounds. Thus, there is a need for a facile in situ method for the generation of a multiplicity of substituted azole derivatives and novel intermediate compounds.

SUMMARY OF THE INVENTION

The present invention is directed to a process for assembly of diverse, 2-substituted azole derivatives and novel intermediate compounds using available azoles as starting materials. The rapid synthesis of such highly complex drug-like molecules is unexpected and surprising.

Accordingly, the invention is directed to a method of synthesizing 2-substituted azole derivatives having the formula (I) or (II):

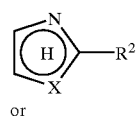

(I)

or

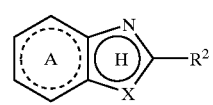

(II)

wherein

X is selected from the group consisting of NH, NR$^A$, and S;

represents a 5 membered aromatic ring structure; optionally containing one to two additional heteroatoms selected from the group consisting of N, O and S;

provided that the additional heteroatoms are not at the attachment point of the R$^2$ group (i.e. the R$^2$ group is always attached to a ring carbon);

provided that the 5 membered ring remains aromatic in nature;

wherein the 5 membered ring is optionally substituted with one to three substituents independently selected from the group consisting of halogen, hydroxy, alkyl, alkenyl, halogenated alkyl, cycloalkyl, alkoxy, aryl, aralkyl, heterocyclyl, amino, mono-or di-substituted amino, cyano, nitro, —COOR, —COR, —SO$_2$R, —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

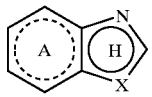

represents a 9 membered ring structure, wherein the five membered portion of the ring structure

is aromatic and the six membered portion of the ring structure

is saturated, partially unsaturated, or aromatic;

wherein the 5 membered portion of the ring structure is optionally substituted with one to two substituents independently selected from the group consisting of halogen, hydroxy, alkyl, alkenyl, halogenated alkyl, cycloalkyl, alkoxy, aryl, aralkyl, heterocyclyl, amino, mono-or di-substituted amino, cyano, nitro, —COOR, —COR, —SO$_2$R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

wherein the 6-membered portion of the ring structure may further optionally containing one to four additional heteroatoms selected from the group consisting of N, O and S;

wherein the 6-membered portion of the ring structure may further be optionally substituted with one to four substituents independently selected from the group consisting of halogen, hydroxy, alkyl, halogenated alkyl, cycloalkyl, alkoxy, aryl, aralkyl, heterocyclyl, amino, mono-or di-substituted amino, cyano, nitro, —COOR, —COR, —SO$_2$R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent independently selected from halogen, hydroxy, alkyl, halogenated alkyl, alkoxy, amino, mono-or di-substituted amino, cyano or nitro;

R$^2$ is selected from the group consisting of

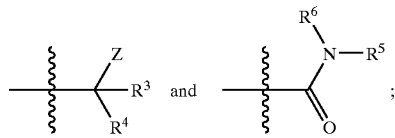

Z is selected from the group consisting of hydrogen, —OR$^A$, —NR$^A$R$^B$,—N(R$^A$)OR$^B$, —SR, —CN, —N$_3$, and

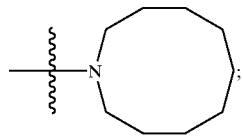

wherein

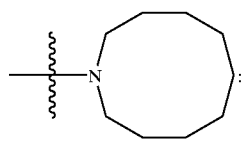

N represents a three to eight membered heterocyclyl group bound at the N atom, wherein the heterocyclyl group is saturated, partially unsaturated or aromatic; when the heterocyclyl group is a saturated six to eight membered heterocyclyl, the heterocyclyl group may optionally contains a group selected from O, CHR, NR, S, SO, or SO$_2$, provided that that the group is separated from the N atom by at least two carbon atoms; and wherein the heterocyclyl group is optionally substituted with one or more substituents independently selected from R;

R$^3$ is selected from the group consisting of hydrogen, alkyl, aralkyl, cycloalkyl, fluorinated alkyl, —COR, —COOR and —CONR$^C$R$^D$; wherein the aralkyl may be optionally substituted with one or more substituents independently selected from halogen, hydroxy, alkyl, halogenated alkyl, alkoxy, amino, mono- or di-substituted amino, cyano or nitro;

R$^4$ is selected from the group consisting of alkyl, aryl, aralkyl, cycloalkyl, fluorinated alkyl, alkenyl, alkynyl, —COOR, —COR, —CONR$^C$R$^D$, -alkyl-COOR, heterocycle and

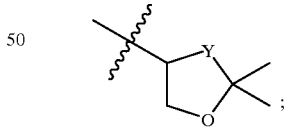

wherein the alkyl, alkenyl, alkynyl, aryl, aralkyl or heterocycle may be optionally substituted with one or more substituents independently selected from halogen, hydroxy, alkyl, halogenated alkyl, alkoxy, aryl, amino, mono-or di-substituted amino, cyano or nitro; wherein Y is selected from the group consisting of O, S and NR$^A$;

R$^5$ is selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

$R^6$ is selected from the group consisting of hydrogen, alkyl, aralkyl, cycloalkyl, —COOR, —COR, —SO$_2$R, —CONR$^C$R$^D$ and

where R is selected from the group consisting of alkyl, aryl, aralkyl, cycloalkyl, adamantyl, norbornyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

where $R^A$ and $R^B$ are independently selected from the group consisting of hydrogen, —R, —COOR, —COR, —SO$_2$R, —SOR and —CONR$^C$R$^D$ and

where $R^C$ and $R^D$ are independently selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro; or are joined together to form a 4 to 8 membered heterocyclyl ring structure;

and pharmaceutically acceptable salt, esters and pro-drugs thereof;

by a facile reaction of an azole compound with a carbamyl chloride followed by reaction in situ with an aldehyde or isocyanate to yield the desired 2-substituted azole.

More particularly, the present invention is directed to a process for preparing compound of the formula (Ia)

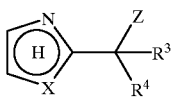
(Ia)

wherein

X is selected from the group consisting of NH, NR$^A$, and S;

represents a 5 membered aromatic ring structure; optionally containing one to two additional heteroatoms selected from the group consisting of N, O and S;

provided that the additional heteroatoms are not at the attachment point of the

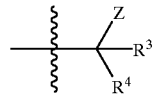

group;

provided that the 5 membered ring remains aromatic in nature;

wherein the 5 membered ring is optionally substituted with one to three substituents independently selected from the group consisting of halogen, hydroxy, alkyl, halogenated alkyl, alkenyl, cycloalkyl, alkoxy, aryl, aralkyl, heterocyclyl, amino, mono-or di-substituted amino, cyano, nitro, —COOR,—COR, —SO$_2$ and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

Z is selected from the group consisting of hydrogen, —OR$^A$, —NR$^A$ R$^B$, —SR, —N(R$^A$)OR$^B$, —CN, —N$_3$ and

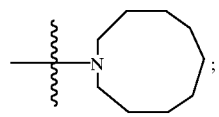

wherein

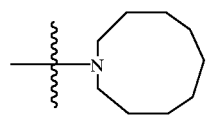

represents a three to eight membered heterocyclyl group bound at the N atom, wherein the heterocyclyl group is saturated, partially unsaturated or aromatic; when the heterocyclyl group is a saturated six to eight membered heterocyclyl, the heterocyclyl group may optionally contains a group selected from O, CHR, NR, S, SO, or SO$_2$, provided that that the group is separated from the N atom by at least two carbon atoms; and wherein the heterocyclyl group is optionally substituted with one or more substituents independently selected from R;

$R^3$ is selected from the group consisting of hydrogen, alkyl, aralkyl, cycloalkyl, fluorinated alkyl, —COR, —COOR and —CONR$^C$R$^D$; wherein the aralkyl may be optionally substituted with one or more substituents independently selected from halogen, hydroxy, alkyl, halogenated alkyl, alkoxy, amino, mono- or di-substituted amino, cyano or nitro;

$R^4$ is selected from the group consisting of alkyl, aryl, aralkyl, cycloalkyl, fluorinated alkyl, alkenyl, alkynyl, —COOR, —COR, —CONR$^C$R$^D$, -alkyl-COOR, heterocyclyl and

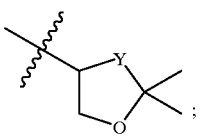

wherein the alkyl, alkenyl, alkynyl, aryl, aralkyl or heterocyclyl may be optionally substituted with one or more substituents independently selected from halogen, hydroxy, alkyl, halogenated alkyl, alkoxy, aryl, amino, mono-or di-substituted amino, cyano or nitro; and where Y is selected from the group consisting of O, S and $NR^A$;

where R is selected from the group consisting of alkyl, aryl, aralkyl, cycloalkyl, adamantyl, norbornyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

where $R^A$ and $R^B$ are independently selected from the group consisting of hydrogen, —R, —COOR, —COR, —$SO_2R$, —SOR and —$CONR^CR^D$ and

where $R^C$ and $R^D$ are independently selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro; or are joined together to form a 4 to 8 membered heterocyclyl ring structure;

which method comprises reacting a compound of formula (III)

(III)

with a compound of formula (IV)

(IV)

wherein A is selected from F, Cl, Br, and —OC(O)-t-butyl and wherein V is a sterically hindered group, in a non-protic solvent;

and then reacting with a compound of formula (V)

(V)

wherein W is selected from the group consisting of —O, —$NSO_2R$, —NSOR, —NCOR, —NCOOR, —$NCONR^CR^D$, —NOCOR and —NR, to form the corresponding compound of formula (Ic)

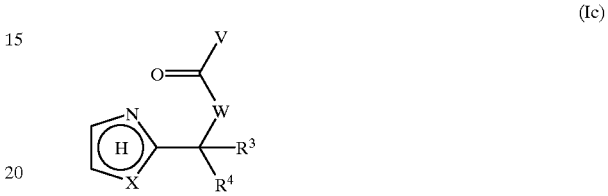

(Ic)

and optionally reacting the compound of formula (Ic) with a compound of formula (VI)

Z—H (VI)

wherein Z is as previously defined, to yield the corresponding compound of formula (Ia).

The present invention is further directed to a process for the synthesis of compounds of the formula (Ib)

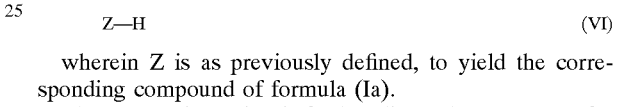

(Ib)

wherein
X is selected from the group consisting of NH, $NR^A$ and S;

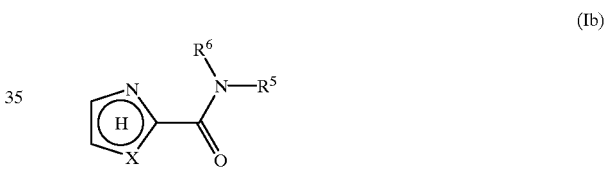

represents a 5 membered aromatic ring structure; optionally containing one to two additional heteroatoms selected from the group consisting of N, O and S;

provided that the additional heteroatoms are not at the attachment point of the —$C(O)NR^5R^6$ group;

provided that the 5 membered ring remains aromatic in nature;

wherein the 5 membered ring is optionally substituted with one to three substituents independently selected from the group consisting of halogen, hydroxy, alkyl, halogenated alkyl, alkenyl, cycloalkyl, alkoxy, aryl, aralkyl, heterocyclyl, amino, mono-or di-substituted amino, cyano, nitro, —COOR, —COR, —$SO_2R$ and —$CONR^BR^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

R⁵ is selected from the group consisting of hydrogen, alkyl, aryl, aralkyl, cycloalkyl, fluorinated alkyl and heterocyclyl; wherein the aryl, aralkyl or heterocyclyl may be optionally substituted with one or more substituents independently selected from halogen, hydroxy, alkyl, halogenated alkyl, alkoxy, amino, mono-or di-substituted amino, cyano or nitro;

R⁶ is selected from the group consisting of hydrogen, alkyl, aralkyl, cycloalkyl, —COOR, —COR, —SO₂R, —CONR^C R^D and

where R is selected from the group consisting of alkyl, aryl, aralkyl, cycloalkyl, adamantyl, norbornyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

where R^A and R^B are independently selected from the group consisting of hydrogen, —R, —COOR, —COR, —SO₂R, —SOR and —CONR^C R^D and

where R^C and R^D are independently selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro; or are joined together to form a 4 to 8 membered heterocyclyl ring structure;

which method comprises reacting a compound of formula (III)

(III)

with a compound of formula (IV)

(IV)

wherein A is selected from F, Cl, Br and —OC(O)-t-butyl, and wherein V is a sterically hindered group, in a non-protic solvent;

and then reacting with a compound of formula (VIII)

R⁵—N=C=O     (VIII)

wherein R⁵ is as previously defined, to yield the compound of formula (Id)

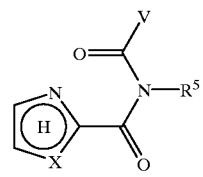

(Id)

reacting the compound of formula (Id) with an inorganic base to yield the compound of formula (Ie)

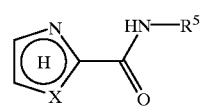

(Ie)

optionally reacting the compound of formula (Ie) with a compound of formula (IX)

R⁶—Q     (IX)

wherein Q is selected from the group consisting of chlorine, bromine and iodine, in the presence of a base, to yield the corresponding compound of formula (Ib).

A further aspect of the present invention is the synthesis of compounds of formula (II):

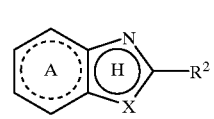

(II)

wherein
X is selected from the group consisting of NH, NR^A and S;

represents a 9 membered ring structure, wherein the five membered portion of the ring structure

is aromatic and the six membered portion of the ring structure

is saturated, partially unsaturated, or aromatic;
wherein the 5 membered portion of the ring structure is optionally substituted with one to two substituents independently selected from the group consisting of halogen, hydroxy, alkyl, alkenyl, halogenated alkyl, cycloalkyl, alkoxy, aryl, aralkyl, heterocyclyl, amino, mono-or di-substituted amino, cyano, nitro, —COOR, —COR, —SO$_2$R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

wherein the 6-membered portion of the ring structure may further optionally containing one to four additional heteroatoms selected from the group consisting of N, O and S;

wherein the 6-membered portion of the ring structure may further be optionally substituted with one to four substituents independently selected from the group consisting of halogen, hydroxy, alkyl, halogenated alkyl, cycloalkyl, alkoxy, aryl, aralkyl, heterocyclyl, amino, mono-or di-substituted amino, cyano, nitro, —COOR, —COR, —SO$_2$R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent independently selected from halogen, hydroxy, alkyl, halogenated alkyl, alkoxy, amino, mono-or di-substituted amino, cyano or nitro;

R$^2$ is selected from the group consisting of

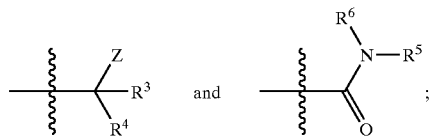

Z is selected from the group consisting of hydrogen, —OR$^A$, —NR$^A$R$^B$, —N(R$^A$)OR$^B$, —SR, —CN, —N$_3$ and

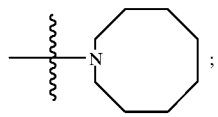

wherein

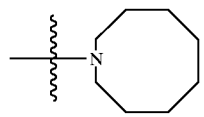

represents a three to eight membered heterocyclyl group bound at the N atom, wherein the heterocyclyl group is saturated, partially unsaturated or aromatic; when the heterocyclyl group is a saturated six to eight membered heterocyclyl, the heterocyclyl group may optionally contains a group selected from O, CHR, NR, S, SO, or SO$_2$, provided that that the group is separated from the N atom by at least two carbon atoms; and wherein the heterocyclyl group is optionally substituted with one or more substituents independently selected from R;

R$^3$ is selected from the group consisting of hydrogen, alkyl, aralkyl, cycloalkyl, fluorinated alkyl, —COR, —COOR and —CONR$^C$R$^D$; wherein the aralkyl may be optionally substituted with one or more substituents independently selected from halogen, hydroxy, alkyl, halogenated alkyl, alkoxy, amino, mono- or di-substituted amino, cyano or nitro;

R$^4$ is selected from the group consisting of, alkyl, aryl, aralkyl, cycloalkyl, fluorinated alkyl, alkenyl, alkynyl, —COOR, —COR, —CONR$^C$R$^D$, -alkyl-COOR, heterocycle and

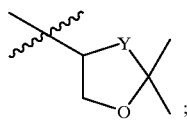

wherein the alkyl, alkenyl, alkynyl, aryl, aralkyl or heterocycle may be optionally substituted with one or more substituents independently selected from halogen, hydroxy, alkyl, halogenated alkyl, alkoxy, aryl, amino, mono-or di-substituted amino, cyano or nitro; wherein Y is selected from the group consisting of O, S and NR$^A$;

R$^5$ is selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

R$^6$ is selected from the group consisting of hydrogen, alkyl, aralkyl, cycloalkyl, —COOR, —COR, —SO$_2$R, —CONR$^C$R$^D$ and

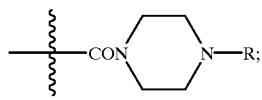

where R is selected from the group consisting of alkyl, aryl, aralkyl, cycloalkyl, adamantyl, norbornyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro;

where R$^A$ and R$^B$ are independently selected from the group consisting of hydrogen, —R, —COOR, —COR, —SO$_2$R, —SOR and —CONRC$^B$R$^D$ and

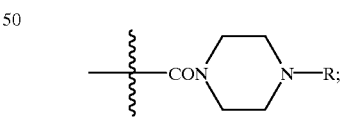

where R$^C$ and R$^D$ are independently selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro; or are joined together to form a 4 to 8 membered heterocyclyl ring structure;

according to either of the processes disclosed herein, with appropriate substitution of a compound of formula (VII)

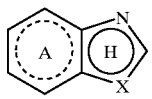

(VII)

for the corresponding monocyclic compound of formula (III)

(III)

DETAILED DESCRIPTION OF THE INVENTION

As used herein, the term "alkyl" whether used alone or as part of a substituent group, shall denote straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1 to 4 carbon atoms. Similarly, as used herein, the term "alkenyl", whether used alone or as part of a substituent group, shall denote straight and branched chain alkene radicals, i.e. straight or branched chains containing at least one double bond. For example, alkenyl radicals include allyl, vinyl, and the like. Similarly, as used herein, the term "alkynyl", whether used alone or as part of a substituent group, shall denote straight and branched chain alkyne radicals, i.e., straight or branched chains containing at least one triple bond. For example, alkynyl radicals include —CCH, —CH$_2$CCH (propargyl), —CH$_2$CCCH$_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, "halogen" shall mean chlorine, bromine, fluorine and iodine.

As used herein, unless otherwise noted, "aryl" shall refer to carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples of aralkyls include benzyl, 1-(phenyl)ethyl, naphthylmethyl, and the like.

As used herein, the term "cycloalkyl" shall denote any monocyclic three to eight membered, saturated carbocyclic ring structure. Suitable examples include cyclopropyl, cyclobutyl, cyclopentyl, cyclohexyl, cycloheptyl and cyclooctyl.

As used herein, unless otherwise noted, the terms "heterocycle", "heterocyclyl" and "heterocyclo" shall denote any five or six membered monocyclic, nine or ten membered bicyclic or thirteen or fourteen membered tricyclic ring structure containing at least one heteroatom selected from the group consisting of N, O and S, optionally containing one to four additional heteroatoms, wherein the ring structure is saturated, partially unsaturated, aromatic or partially aromatic. The heterocyclyl group may be attached at any heteroatom or carbon atom which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropryanyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, triazinyl, triazolyl and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl and the like.

Exemplary tricyclic heterocylclic groups include phenoxazinyl, phenazinyl, phenothiazinyl, carbozolyl, perminidinyl, phenanthrolinyl, carbolinyl, naphthothienyl, thianthrenyl, and the like.

In the definition of Z, suitable examples of the

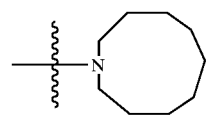

group include pyrazol-1-yl, imidazol-1-yl, pyrrol-1-yl, 1,2,4-triazol-1-yl, 1,2,4-triazol-4-yl, 1,2,3-triazol-1-yl, aziridin-1-yl, pyrrolidin-1-yl, piperidin-1yl, piperazin-1-yl, morpholin-1-yl, 4-methyl-diazepin-1-yl, azepin-1-yl, diazepin-1-yl, 4-methyl-piperazin-1-yl, and the like.

When a particular group is "substituted" (e.g., cycloalkyl, aryl, heterocyclyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylalkylaminocarbonylalkyl" substituent refers to a group of the formula

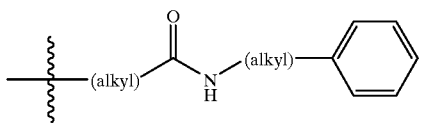

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of this invention, the term "chemical library" means a collection of molecules prepared by the method of the invention based on logical design by means of simultaneous or parallel chemical reactions. Each species of molecule in the library is referred to as a member of the library.

Abbreviations used in the specification, particularly the Schemes and Examples, are as follows:

| | |
|---|---|
| DIPEA = | Diisopropylethylamine |
| DMF = | N,N-Dimethylformamide |
| Et = | Ethyl (—CH$_2$CH$_3$) |
| Ex # = | Example Number |
| Me = | Methyl (—CH$_3$) |
| Pd(PPh$_3$)$_4$ = | Palladium, tetrakis(triphenylphosphine)- |
| Ph = | Phenyl (—C$_6$H$_5$) |
| TEA = | Triethylamine |
| TFA = | Trifluoroacetic acid |
| THF = | Tetrahydrofuran |

Compounds of formula (Ia), compounds of formula (I) wherein R$^2$ is

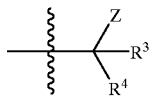

may be prepared using solution phase chemistry according to the process outlined in Scheme 1.

SCHEME 1

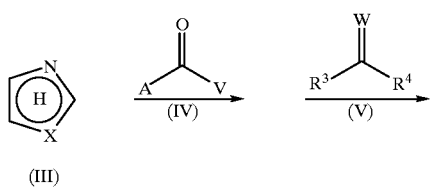

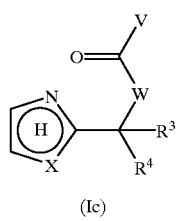

(Ic)

Accordingly, a compound of formula (III), a known compound or compound prepared by known methods, is reacted sequentially with a compound of formula (IV), wherein A is selected from F, Cl, Br or —OC(O)-t-butyl and wherein V is a sterically hindered group such as t-butyl, adamantyl, N(alkyl)$_2$, N(aryl)$_2$, 2,6-dimethylphenyl, 2,6-disubstituted phenyl, O-t-butyl, O-isopropyl, O-adamantyl, and the like, at a temperature in the range of about 0° C. to about reflux in a non-protic solvent such as acetonitrile, dioxane, THF, and the like;

and then reacted with a compound of formula (V), wherein W is —O, —NSO$_2$R, —NSOR, —NCOR, —NCOOR, —NCONR$^C$R$^D$, —NOCOR or —NR, in the presence of an organic base such as TEA, DIPEA, and the like, to yield the corresponding compound of formula (Ic).

Compounds of formula (Ic) wherein W is O may be further converted to compounds of formula (Ia), wherein Z is not hydrogen, according to the process outlined in Scheme 2.

Scheme 2

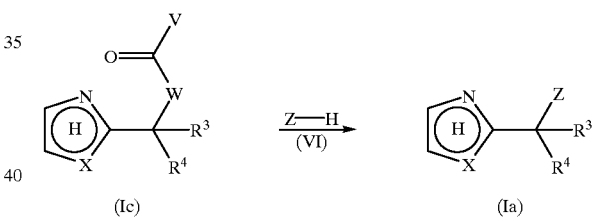

Accordingly, the compound of formula (Ic) is reacted with a compound of formula (VI), in a non-protic solvent such as acetonitrile, dioxane, THF, and the like, in the presence of an acid such as TFA, and the like, at a temperature in the range of about 0° C. to about reflux, preferably at about reflux temperature, to form the corresponding compound of formula (Ia).

When in the compound of formula (Ia) Z is H, the compound of formula (Ic) is reduced by hydrogenation with a metal catalyst such as palladium, platinum, palladium on carbon, and the like, in an organic solvent such as methanol, ethanol, ethyl acetate, acetic acid, THF, DMF, and the like, to form the corresponding compound of formula (Ia).

Similarly, compounds of formula (II) wherein R$^2$ is

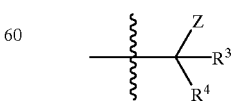

may be prepared according to the process as outlined in Schemes 1&2, with appropriate substitution of a compound of formula (VII)

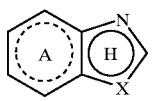
(VII)

for the compound of formula (III), to yield the corresponding compound of formula (IIa)

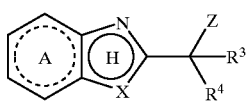
(IIa)

Compounds of formula (I) wherein $R^2$ is

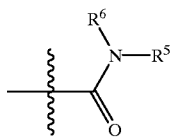

may be prepared according to the process outlined in Scheme 3.

Scheme 3

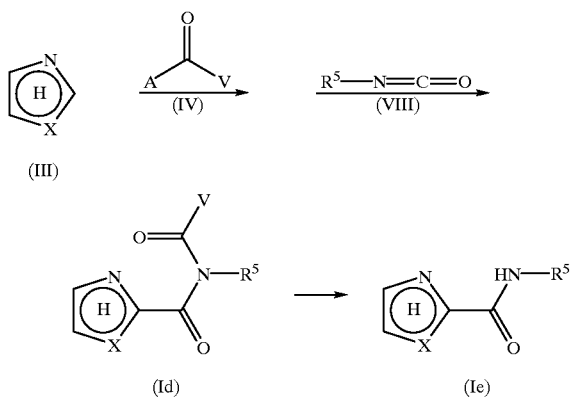

More specifically, a compound of formula (III), a known compound or compound prepared by known methods, is reacted sequentially with a compound of formula (IV), wherein A is selected from F, Cl, Br or —OC(O)-t-butyl, and wherein V is a sterically hindered group such as t-butyl, adamantyl, N(alkyl)$_2$, N(aryl)$_2$, 2,6-dimethylphenyl, 2,6-disubstituted phenyl, O-t-butyl, O-isopropyl, O-adamantyl, and the like, at a temperature in the range of about 0° C. to about reflux, preferably a about reflux temperature, in a non-protic solvent such as acetonitrile, dioxane, THF, and the like;

and then reacted with a suitably substituted isocyanate of formula (VIII), in the presence of a base such as TEA, DIPEA, and the like, at a temperature in the range of about 0° C. to about reflux, preferably at about reflux temperature, to form the corresponding compound of formula (Id).

The compound of formula (Id) is further optionally reacted with an inorganic base such as sodium hydroxide, to form the corresponding compound of formula (Ie). Alternatively, the compound of formula (Id) is further optionally reacted with an inorganic base such as potassium carbonate, sodium carbonate, and the like, in the presence of water, to form the corresponding compound of formula (Ie).

The compound of formula (Ie) is optionally further reacted to form the compound of formula (1b) according to the process outlined in Scheme 4.

Scheme 4

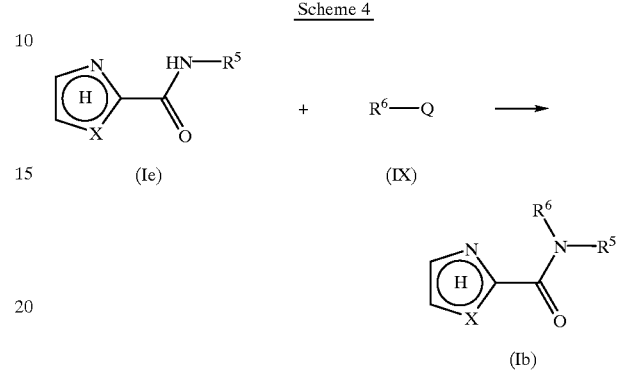

Accordingly, the compound of formula (Ie) is reacted with a compound of formula (IX), wherein Q is selected from the group consisting of chlorine, bromine and iodine, in the presence of a base such as NaH, potassium t-butoxide, potassium carbonate, and the like, to yield the corresponding compound of formula (Ib).

Similarly, compounds of formula (II) wherein $R^2$ is

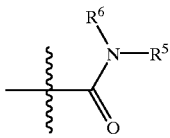

may be prepared using the solution phase chemistry outlined in Scheme 5, with appropriate substitution of a compound of formula (VII)

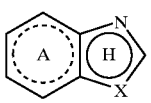
(VII)

for the compound of formula (III), to produce the corresponding compound of formula (IIb).

(IIb)

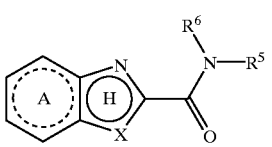

The following Examples are set forth to aid in the understanding of the invention, and are not intended and should not be construed to limit in any way the invention set forth in the claims which follow thereafter.

EXAMPLE 1

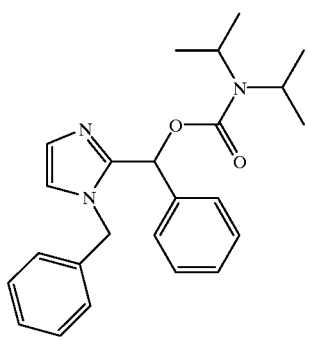

To a suspension of 1-benzylimidazole (315 mg, 2.0 mmol) in acetonitrile (3 mL) at 0° C. and under nitrogen was added rapidly dropwise a solution of diisopropylcarbamyl chloride (396 mg, 2.4 mmol) in acetonitrile (5 mL). To the slightly cloudy solution was added benzaldehyde (0.31 mL, 3.0 mmol), followed by N,N-diisopropylethylamine (1.1 mL, 6.3 mmol). The ice bath was removed and after stirring for 10 min, the cloudy yellow solution was refluxed for 24 h, cooled to room temperature, and concentrated in vacuo. The residue was dissolved in ethyl acetate and washed successively with 2N NaOH, water, and saturated brine. The organic layer was dried over magnesium sulfate, filtered, and concentrated to yield a pale yellow oil (1.01 g). Flash chromatography on silica (50 mm×7 in) eluted with ethyl acetate-hexanes (1:1) yielded the product as white crystals.

Yield: 611 mg, 78% mp 106–109° C.;

MS (ESP) m/z 392 (MH$^+$)

EXAMPLE 2

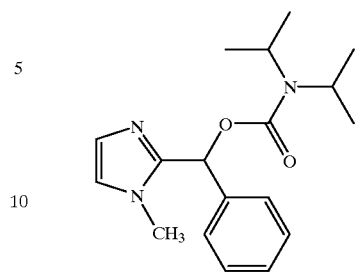

To a solution of 1-methylimidazole (1.64 g, 20 mmol) and diisopropylcarbamyl chloride (3.6 g, 22 mmol) in acetonitrile (30 mL) at room temperature and under nitrogen was added dropwise benzaldehyde (3.1 mL, 30 mmol), followed by N,N-diisopropylethylamine (10 mL, 60 mmol). The resulting mixture was stirred at room temperature for 24, and then concentrated in vacuo. The residue was purified by flash chromatography on silica (BIOTAGE, FLASH 40i, Charlottesville, Va., USA) eluted with ethyl acetate-hexanes (1:1) to yield the title product as white crystals.

Yield: 6 g, 95% mp 67–68° C.;

MS (ESP) m/z 317 (MH$^+$)

EXAMPLES 3–29

Selected compounds listed in Table 1 were similarly prepared following the procedure outlined in Example 1 and Example 2, with appropriate selection substitution of reagents, as listed in Table 2.

TABLE 1

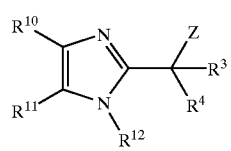

| Ex # | $R^{10}$ | $R^{11}$ | $R^{12}$ | Z | $R^3$ | $R^4$ |
|---|---|---|---|---|---|---|
| 3 | H | H | benzyl | OC(O)N(i-propyl)$_2$ | H | t-butyl |
| 4 | H | H | benzyl | OC(O)N(i-propyl)$_2$ | H | i-propyl |
| 5 | H | H | benzyl | OC(O)N(i-propyl)$_2$ | H | cyclohexyl |
| 6 | H | H | benzyl | OC(O)N(i-propyl)$_2$ | H | phenylethyl |
| 7 | H | H | benzyl | OC(O)N(i-propyl)$_2$ | H | benzyl |
| 8 | H | H | benzyl | OC(O)N(i-propyl)$_2$ | H | 4-methoxyphenyl |
| 9 | H | H | benzyl | OC(O)N(i-propyl)$_2$ | H | 4-methoxyphenyl |
| 10 | H | H | benzyl | OC(O)N(i-propyl)$_2$ | H | 4-chlorophenyl |
| 11 | H | H | benzyl | OC(O)N(i-propyl)$_2$ | CF$_3$ | phenyl |
| 12 | H | H | benzyl | OC(O)N(i-propyl)$_2$ | —C(O)O—CH$_2$CH$_3$ | 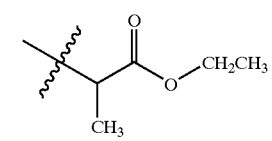 |

TABLE 1-continued

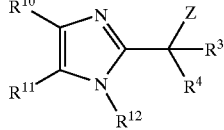

| Ex # | R10 | R11 | R12 | Z | R3 | R4 |
|---|---|---|---|---|---|---|
| 13 | H | H | benzyl | OC(O)N(i-propyl)$_2$ | H | —CH=CH$_2$ |
| 14 | H | H | benzyl | OC(O)N(i-propyl)$_2$ | H | 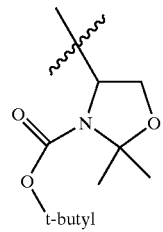 |
| 15 | H | H | benzyl | OC(O)N(i-propyl)$_2$ | H | 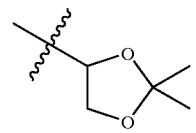 |
| 16 | H | H | benzyl | N(phenyl)-C(O)-N(i-propyl)$_2$ | H | phenyl |
| 17 | H | H | benzyl | N(SO$_2$phenyl)-C(O)-N(i-propyl)$_2$ | H | phenyl |
| 18 | H | H | methyl | —OC(O)N(i-propyl)$_2$ | H | phenyl |
| 19 | H | Cl | methyl | —OC(O)N(i-propyl)$_2$ | H | phenyl |
| 20 | H | H | Phenyl | —OC(O)N(i-propyl)$_2$ | H | phenyl |
| 21 | Cl | Cl | methyl | —OC(O)N(i-propyl)$_2$ | H | phenyl |
| 22 | H | H | methyl | —OC(O)N(ethyl)$_2$ | H | phenyl |
| 23 | H | H | methyl | —OC(O)N(methyl)$_2$ | H | phenyl |
| 24 | H | H | methyl | —OC(O)N(i-propyl)$_2$ | H | ethyl |
| 25 | H | H | methyl | —OC(O)N(i-propyl)$_2$ | H | —CH=CHCH$_3$ |
| 26 | H | H | methyl | —OC(O)N(methyl)$_2$ | H | 2-pyridinyl |
| 27 | H | H | methyl | —OC(O)N(methyl)$_2$ | H | -C(O)-phenyl |
| 28 | H | H | methyl | —OC(O)N(methyl)$_2$ | -C(O)O-CH$_2$CH$_3$ | phenylethyl |
| 29 | H | C(O)OCH$_3$ | methyl | —OC(O)N(methyl)$_2$ | H | phenyl |

TABLE 2

Preparation Conditions

| Ex # | Reaction Temp (° C.) | Reflux Time (h) | Yield (%) | mp (° C.) | mass spec (MH$^+$) |
|---|---|---|---|---|---|
| 3 | reflux | 24 | 66 | 48–52 | 372 |
| 4 | room temp | 66 | 85 | oil | 358 |
| 5 | room temp | 24 | 56 | oil | 398 |
| 6 | room temp | 29 | 75 | 73–78 | 420 |
| 7 | reflux | 20 | 32 | oil | 406 |
| 8 | reflux | 21 | 30 | oil | 277 M$^+$ w/loss of OC(O)(i-propyl)$_2$ |
| 9 | room temp | 67 | 73 | oil | 277 M$^+$ w/loss of OC(O)(i-propyl)$_2$ |
| 10 | room temp | 30 | 77 | 113–115 | 426 |
| 11 | room temp | 72 | 89 | 124–126 | 460 |
| 12 | room temp | 68 | 73 | oil | 488 |
| 13 | room temp | 68 | 67 | oil | 342 |
| 14 | room temp | 72 | 76 | oil | 515 |
| 15 | room temp | 144 | 79 | oil | 416 |
| 16 | reflux | 21 | 12 | oil | 467 |
| 17 | room temp | 72 | 88 | 132–139 | 531 |
| 18 | room temp | 24 | 90 | 67–68 | 316 |
| 19 | 50 | 24 | 66 | oil | 350 |
| 20 | room temp | 24 | 86 | 104–105 | 378 |
| 21 | reflux | 20 | 42 | 118–118.5 | 384 |
| 22 | 60 | 20 | 91 | oil | 288 |

TABLE 2-continued

| | Preparation Conditions | | | | |
|---|---|---|---|---|---|
| Ex # | Reaction Temp (° C.) | Reflux Time (h) | Yield (%) | mp (° C.) | mass spec (MH$^+$) |
| 23 | 60 | 20 | 93 | 102–102 | 260 |
| 24 | room temp | 48 | 96 | oil | 268 |
| 25 | room temp | 48 | 65 | oil | 280 |
| 26 | room temp | 20 | 78 | oil | 261 |
| 27 | room temp | 20 | 70 | 92–93 | 288 |
| 28 | room temp | 20 | 60 | 112–113 | 360 |
| 29 | room temp | 48 | 80 | 134–135 | 318 |

EXAMPLES 30–32

Selected compounds listed in Table 3 were similarly prepared following the procedure outlined in Example 1, with appropriate selection and substitution of reagents, as listed in Table 4. Note that the conditions as disclosed in Example 31 yielded a mixture of compounds are defined below.

TABLE 3

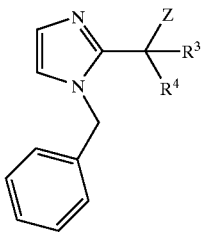

| Ex # | Z | R$^3$ | R$^4$ |
|---|---|---|---|
| 30 | —OC(O)O(t-butyl) | H | phenyl |
| 31 | —OC(O)O(t-butyl) | H | phenyl |
|    | —OC(O)(phenyl) | H | phenyl |
| 32 | —OC(O)(t-butyl) | H | phenyl |

TABLE 4

| | Preparation Conditions | | | | |
|---|---|---|---|---|---|
| Ex # | Reaction T (° C.) | Reflux Time (h) | Yield (%) | mp (° C.) | mass spec (MH$^+$) |
| 30 | room temp | 23 | 44 | 77–79 | 365 |
| 31 | reflux | 21 | 52 | 75–79 | 365 |
|    |         |    | 11 | oil   | 369 |
| 32 | reflux | 21 | 32 | oil | 349 |

EXAMPLE 33

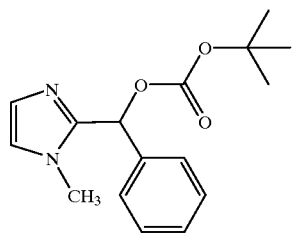

To a solution of 1-methylimidazole (164 mg, 2.0 mmol) in anhydrous acetonitrile (5 mL) at room temperature and under nitrogen was added dropwise benzaldehyde (0.31 mL, 3.0 mmol) and a solution of di-tert-butyl dicarbonate (480 mg, 2.2 mmol) in anhydrous acetonitrile (1 mL). The mixture was stirred at room temperature for 3 hours, then concentrated in vacuo. The residue was purified by flash chromatography on silica eluted with ethyl acetate-hexanes (2:3) to yield the title product as white crystals.

Yield: 421 mg, 77% mp 95–96° C.;

MS (ESP) m/z 289 (MH$^+$)

EXAMPLE 34

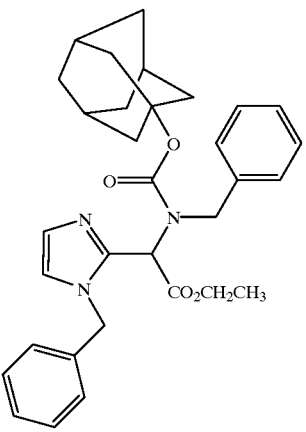

To a solution of 1-benzylimidazole (313 mg, 2.0 mmol) in anhydrous acetonitrile (2 mL) at room temperature and under nitrogen was added dropwise a solution of adamantylfluoroformate (498 mg, 2.5 mmol) in anhydrous acetonitrile (2 mL), a solution of benzyliminoacetic acid ethyl ester (573 mg, 3.0 mmol) in anhydrous acetonitrile (2 mL), and diisopropylethyl amine (1.1. mL, 6.3 mmol). The mixture was stirred at room temperature for 16 hours, then concentrated in vacuo. The residue was purified by flash chromatography on silica eluted with ethyl acetate-hexanes (1:3) to yield the title product as white crystals.

Yield: 441 mg, 42% mp 83–85° C.;

MS (ESP) m/z 538 (MH$^+$)

EXAMPLES 35–40

Selected compounds listed in Table 5 were similarly prepared following the procedure outlined in Example 1, Example 2 and Example 33 with appropriate selection and substitution of reagents, as listed in Table 6.

TABLE 5

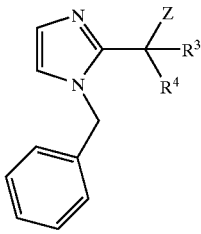

| Ex # | Z | R³ | R⁴ |
|---|---|---|---|
| 35 | —N(C(O)N(i-propyl)₂)OC(O)CH₃ | H | phenyl |
| 36 | —N(benzyl)C(O)N(i-propyl)₂ | H | phenyl |
| 37 | —N(benzyl)C(O)N(i-propyl)₂ | H | phenyl |
| 38 | —N(SO₂phenyl)C(O)O-t-butyl | H | phenyl |
| 39 | —N(SO₂-p-toluenyl)C(O)O-t-butyl | methyl | phenyl |
| 40 | —N(benzyl)C(O)O-t-butyl | H | —C(O)O-ethyl |

TABLE 6

| Ex # | Reaction T (° C.) | Reaction Time (h) | Yield (%) | mp (° C.) | mass spec (MH⁺) |
|---|---|---|---|---|---|
| 35 | room temp | 16 | 60 | oil | 248 M⁺ w/loss of C(O)N(i-propyl)₂ |
| 36 | room temp | 15 | 65 | oil | 248 M⁺ w/loss of C(O)N(i-propyl)₂ |
| 37 | room temp | 15 | 45 | oil | 248 M⁺ w/loss of C(O)N(i-propyl)₂ |
| 38 | room temp | 3 | 60 | 51–52 | 503 |
| 39 | room temp | 3 | 35 | 56–57 | 531 |
| 40 | room temp | 3 | 55 | oil | 449 |

EXAMPLES 41–50

Selected compounds listed in Table 7 and Table 8 were similarly prepared following the procedure outlined in Example 1, Example 2 and Example 33, with appropriate selection and substitution of reagents, as listed in Table 9

TABLE 7

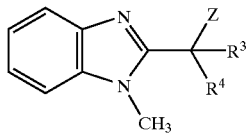

| Ex # | Z | R | R |
|---|---|---|---|
| 41 | OC(O)N(i-propyl)₂ | H | phenyl |

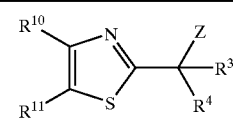

| Ex # | Z | R¹⁰ | R¹¹ | R³ | R⁴ |
|---|---|---|---|---|---|
| 42 | OC(O)N(i-propyl)₂ | H | H | H | phenyl |
| 43 | —OC(O)N(i-propyl)₂ | H | H | H | phenyl |
| 44 | —OC(O)N(i-propyl)₂ | H | H | H | p-nitrophenyl |
| 45 | —OC(O)N(i-propyl)₂ | H | H | CF₃ | phenyl |
| 46 | —OC(O)N(i-propyl)₂ | CH₃ | CH=CH₂ | H | phenyl |
| 47 | —OC(O)N(i-propyl)₂ | CH₃ | CH₃ | H | phenyl |

TABLE 7-continued

| 48 | —OC(O)O-t-butyl | H | H | H | phenyl |
|---|---|---|---|---|---|
| 49 | —OC(O)NMe2 | H | H | H | phenyl |

TABLE 8

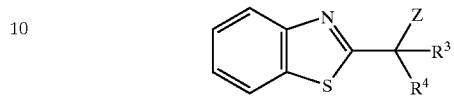

| Ex # | Z | R³ | R⁴ |
|---|---|---|---|
| 50 | —OC(O)N(methyl)₂ | H | phenyl |

TABLE 9

| | Preparation Conditions | | | | |
|---|---|---|---|---|---|
| Ex # | Reaction T (° C.) | Reflux Time (h) | Yield (%) | mp (° C.) | mass spec (MH⁺) |
| 41 | reflux | 23 | 88 | 126–128 | 366 |
| 42 | reflux | 22 | 39 | 70–71 | 319 |
| 43 | reflux | 52 | 17 | 65–68 | 319 |
| 44 | room temp | 48 | 42 | oil | 364 |
| 45 | room temp | 48 | 55 | 82–82 | 387 |
| 46 | reflux | 24 | 42 | oil | 359 |
| 47 | reflux | 24 | 46 | 98–99 | 347 |
| 48 | 60 | 20 | 65 | oil | 292 |
| 49 | 60 | 20 | 61 | 45–47 | 263 |
| 50 | 60 | 20 | 41 | oil | 313 |

EXAMPLES 51–52

Selected compounds listed in Table 10 were similarly prepared following the procedure outlined in Example 2, with appropriate selection and substitution of reagents, as listed in Table 11.

TABLE 10

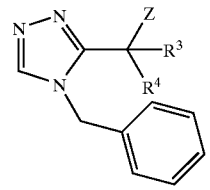

| Ex # | Z | R³ | R⁴ |
|---|---|---|---|
| 51 | —OC(O)N(i-propyl)₂ | H | phenyl |
| 52 | —OC(O)N(i-propyl)₂ | H | phenyl |

TABLE 11

| | Preparation Conditions | | | | |
|---|---|---|---|---|---|
| Ex # | Reaction T (° C.) | Time (h) | Yield (%) | mp (° C.) | mass spec (MH⁺) |
| 51 | room temp | 23 | 68 | 115–116 | 393 |
| 52 | room temp | 22 | 66 | 93–94 | 393 |

EXAMPLE 53

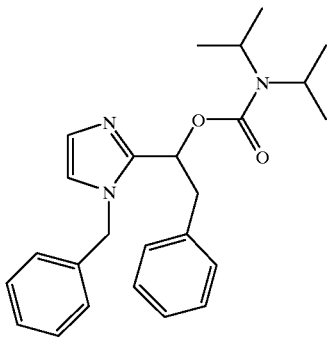

To a suspension of 1-benzylimidazole (317 mg, 2.0 mmol) in acetonitrile (3 mL) at room temperature was added rapidly dropwise a solution of diisopropylcarbamyl chloride (396 mg, 2.4 mmol) in acetonitrile (5 mL). To the slightly cloudy solution was added phenylacetaldehyde (0.35 mL, 3.0 mmol), followed by N,N-diisopropylethylamine (1.1 mL, 6.3 mmol). The mixture was refluxed for 5.5 h and cooled to room temperature. To the resulting mixture was then added a solution of diisopropylcarbamyl chloride (396 mg, 2.4 mmol) in acetonitrile (5 mL), followed by phenylacetaldehyde (0.35 mL, 3.0 mmol) and N,N-diisopropylethylamine (1.1 mL, 6.3 mmol). The reaction mixture was refluxed for 24 h, cooled to room temperature, and then charged again with a solution of diisopropylcarbamyl chloride (396 mg, 2.4 mmol) in acetonitrile (5 mL), followed by phenylacetaldehyde (0.35 mL, 3.0 mmol) and N,N-diisopropylethylamine (1.1 mL, 6.3 mmol). The mixture was refluxed for an additional 21 h, cooled to room temperature, and concentrated in vacuo. The residue was dissolved in ethyl acetate and washed successively with 2N NaOH, water, and saturated brine. The organic layer was dried over magnesium sulfate, filtered, and concentrated to a yellow oil (2.70 g). Flash chromatography on silica (50 mm×8 in) eluted with 40% ethyl acetate in hexanes yielded the product as pale yellow crystals.

Yield: 632 mg, 78% mp 75–79° C.;

MS (ESP) m/z 406 (MH$^+$)

EXAMPLE 54

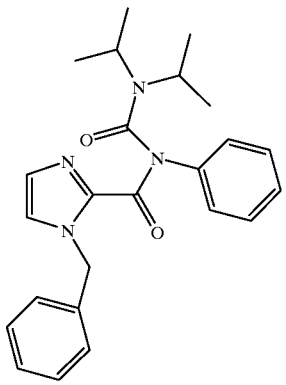

To a suspension of 1-benzylimidazole (317 mg, 2.0 mmol) in acetonitrile (3 mL) at room temperature and under nitrogen was added rapidly dropwise a solution of diisopropylcarbamyl chloride (391 mg, 2.4 mmol) in acetonitrile (5 mL). To the slightly cloudy solution was added phenylisocyanate(0.33 mL, 3.0 mmol), followed by N,N-diisopropylethylamine (1.1 mL, 6.3 mmol). The mixture was refluxed for 21 h, cooled to room temperature, and concentrated in vacuo. The residue was dissolved in ethyl acetate and washed successively with 2N NaOH, water, and saturated brine. The organic layer was dried over magnesium sulfate, filtered, and concentrated to yield a yellow oil (1.22 g). Flash chromatography on silica (50 mm×6 in) eluted with 25% ethyl acetate in hexanes yielded a crystalline solid product (1.0 g) containing an impurity. Flash chromatography of this material on silica (50 mm×6 in) eluted with 20% acetone in hexanes yielded a pale yellow foam (825 mg). The foam was recrystallized from ethyl acetate/hexanes to yield the title product as white crystals.

Yield: 577 mg, 71% mp 125.5–127° C.;

MS (ESP) m/z 405 (MH$^+$)

EXAMPLE 55

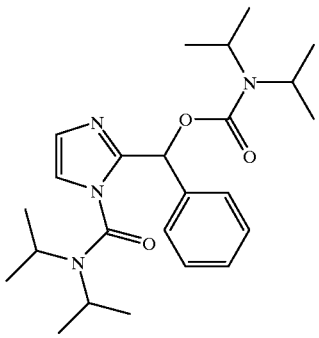

To a suspension of imidazole (140 mg, 2.0 mmol) in acetonitrile (3 mL) at room temperature and under nitrogen was added rapidly dropwise a solution of diisopropylcarbamyl chloride (786 mg, 4.8 mmol) in acetonitrile (5 mL). To the mixture was added benzaldehyde (0.31 mL, (3.0 mmol), followed by N,N-diisopropylethylamine (1.5 mL, 8.6 mmol). The reaction mixture was refluxed for 22 h, cooled to room temperature, and concentrated in vacuo. The residue was dissolved in ethyl acetate and washed successively with dilute brine (2×) and saturated brine. The organic layer was dried over magnesium sulfate, filtered, and concentrated to a yellow solid (1.19 g). Flash chromatography on silica (50 mm×6 in) eluted with 45% ethyl acetate in hexanes yielded the product as white crystals.

Yield: 536 mg, 61% mp 173–175° C.;

MS (ESP) m/z 429 (MH$^+$)

EXAMPLE 56

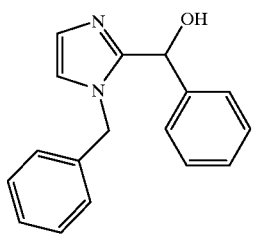

A solution of the product prepared in Example 1 (392 mg 1.0 mmol) in tetrahydrofuran (5 mL), water (1 mL), and trifluoroacetic acid (0.5 mL) was refluxed for 11 h. After cooling, the reaction mixture was diluted with 1:1 ethyl acetate/ethyl ether and washed successively with 2N NaOH, water, and saturated brine. The organic layer was dried over magnesium sulfate, filtered, and concentrated to yield a white solid. Flash chromatography on silica (25 mm×7 in) eluted with 5% methanol in methylene chloride yielded the product as white crystals.

Yield: 222 mg, 84% mp 111–114° C.;

MS (ESP) m/z 265 (MH$^+$)

EXAMPLE 57

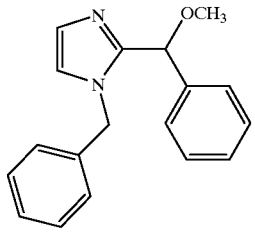

A solution of the product prepared in Example 1 (391 mg, 1.0 mmol) in anhydrous methanol (5 mL) and trifluoroacetic acid (0.5 mL) under a nitrogen atmosphere was refluxed for 28 h. After cooling, trifluoroacetic acid (0.5 mL) was added and the refluxing continued for 24 h. After cooling, the reaction mixture was diluted with 1:1 ethyl acetate/ethyl ether and washed successively with 2N NaOH, water, and saturated brine. The organic layer was dried over magnesium sulfate, filtered, and concentrated to yield a white film. Flash chromatography on silica (25 mm×7 in) eluted with 80% ethyl acetate in hexanes yielded the product as pale yellow crystals.

Yield: 167 mg, 60% mp 68–71.5° C.;

MS (ESP) m/z 279 (MH$^+$)

EXAMPLE 58

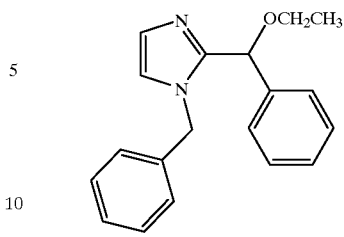

A solution of the product prepared in Example 1 (781 mg, 2.0 mmol) in anhydrous ethanol (10 mL) and trifluoroacetic acid (0.5 mL) under a nitrogen atmosphere was refluxed for 8 h. After cooling, the reaction mixture was concentrated, diluted with ethyl acetate and then washed successively with 2N NaOH, water, and saturated brine. The organic layer was dried over magnesium sulfate, filtered, and concentrated to yield a yellow oil (0.77 g). Flash chromatography on silica (50 mm×6 in) eluted with 60% ethyl acetate in hexanes yielded the product as a colorless oil.

Yield: 492 mg, 84%

MS (ESP) m/z 293 (MH$^+$)

EXAMPLE 59

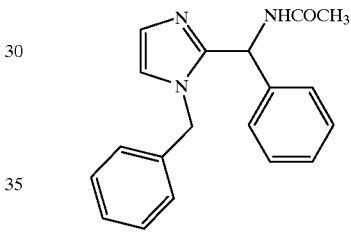

A solution of the product prepared in Example 1 (787 mg, 2.0 mmol) and acetamide (1.18 g, 20 mmol) in tetrahydrofuran (10 mL) and trifluoroacetic acid (0.5 mL) under a nitrogen atmosphere was refluxed for 18 h. After cooling, the reaction mixture was diluted with 1:1 ethyl acetate/ethyl ether and washed successively with 2N NaOH, water, and saturated brine. The organic layer was dried over magnesium sulfate, filtered, and concentrated to yield a white solid (555 mg). The solid was recrystallized from ethyl acetate/hexanes to yield the title product as white crystals.

Yield: 385 mg, 63% mp 171–176° C.;

MS (ESP) m/z 306 (MH$^+$)

EXAMPLE 60

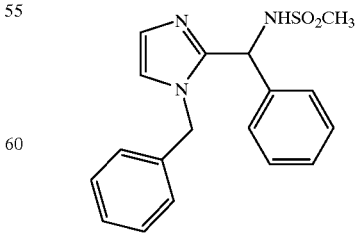

A solution of the product prepared in Example 1 (784 mg, 2.0 mmol) and methanesulfonamide (1.90 g, 20 mmol) in tetrahydrofuran (10 mL) and trifluoroacetic acid (0.5 mL) under a nitrogen atmosphere was refluxed for 24 h. After cooling, the reaction mixture was concentrated, diluted with 1:1 ethyl acetate/ethyl ether and then washed successively with 1N sodium carbonate, water, and saturated brine. The organic layer was dried over magnesium sulfate, filtered, and concentrated to yield a white film (0.75 g). Flash chromatography on silica (50 mm×6 in) eluted with 4% methanol in methylene chloride yielded the product as white crystals.

Yield: 514 mg, 75% mp 162–163° C.;

MS (ESP) m/z 342 (MH$^+$)

EXAMPLE 61

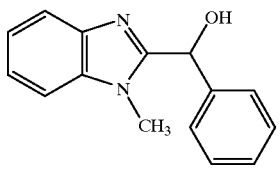

A solution of the product prepared in Example 40 (364 mg, 1.0 mmol) in tetrahydrofuran (5 mL), water (1 mL) and trifluoroacetic acid (0.5 mL) was refluxed for 18 h. After cooling, the reaction mixture was diluted with ethyl acetate and washed successively with 1N sodium carbonate, water, and saturated brine. The organic layer was dried over magnesium sulfate, filtered, and concentrated to yield white crystals. Flash chromatography on silica (25 mm×8 in) eluted with 3% methanol in methylene chloride yielded the product as white crystals.

Yield: 148 mg, 62% mp 160.5–162° C.;

MS (ESP) m/z 239 (MH$^+$)

EXAMPLE 62

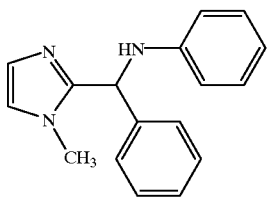

To a solution of the product prepared in Example 2 (158 mg, 0.5 mmol) in anhydrous THF (5 mL) and trifluoroacetic acid (0.22 mL, 3 mmol) under a nitrogen atmosphere was added aniline (0.47 mL, 5 mmol). The resulting mixture was refluxed for 4 h. After cooling, the reaction mixture was diluted with dichloromethane and washed successively with 2N NaOH, water, and saturated brine. The organic layer was dried over magnesium sulfate, filtered, and concentrated to yield a yellow oil. Flash chromatography on silica (20 mm×6 in) eluted with 50% ethyl acetate in hexanes yielded the product as light yellow crystals.

Yield: 102 mg, 81% mp 110–112° C.;

MS (ESP) m/z 264 (MH$^+$)

EXAMPLE 63

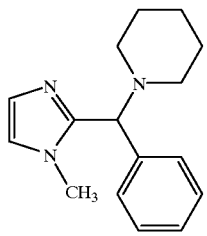

To a solution of the product prepared in Example 2 (158 mg, 0.5 mmol) in anhydrous THF (5 mL) and trifluoroacetic acid (0.33 mL, 4.5 mmol) under a nitrogen atmosphere was added piperidine (0.5 mL, 5 mmol) and BF$_3$19 Et$_2$O (0.1 mL, 0.75 mmol) successively. The resulting mixture was refluxed for 4. After cooling, the reaction mixture was diluted with dichloromethane and washed successively with 2N NaOH, water, and saturated brine. The organic layer was dried over magnesium sulfate, filtered, and concentrated to yield a yellow oil. Flash chromatography on silica (20 mm×6 in) eluted with 5% methanol in ethyl acetate yielded the product as a light yellow oil.

Yield: 109 mg, 85%

MS (ESP) m/z 256 (MH$^+$)

EXAMPLE 64

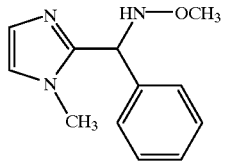

To a suspension of the product prepared in Example 2 (158 mg, 0.5 mmol) and H$_2$NOMe·HCl (555 mg, 5 mmol) in anhydrous THP (5 mL) under a nitrogen atmosphere was added BF$_3$·Et$_2$O (0.2 mL, 1.5 mmol). The resulting mixture was refluxed for 4. After cooling, the reaction mixture was filtered. The filtrate was dissolved in 10% methanol in dichloromethane, and washed successively with saturated NaHCO$_3$, water, and saturated brine. The organic layer was dried over magnesium sulfate, filtered, and concentrated to yield a yellow oil. Flash chromatography on silica (20 mm×6 in) eluted with 10% methanol in dichloromethane yielded the product as white crystals.

Yield: 80 mg, 73% mp 119–122° C.;

MS (ESP) m/z 218 (MH$^+$)

EXAMPLE 65

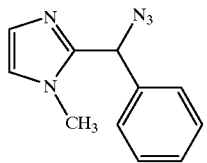

To a solution of the product prepared in Example 2 (158 mg, 0.5 mmol) in anhydrous DMF (5 mL) under a nitrogen atmosphere was added NaN₃ (98 mg, 1.5 mmol) and pyridinium p-toluenesufonate (catalytic amount). The resulting mixture was stirred at 70° C. overnight. After cooling, the reaction mixture was diluted with dichloromethane and washed successively with saturated NaHCO₃, water, and saturated brine. The organic layer was dried over magnesium sulfate, filtered, and concentrated to yield a yellow oil. Flash chromatography on silica (20 mm×6 in) eluted with 2% methanol in ethyl acetate yielded the product as a oil.

Yield: 85 mg, 80%

MS (ESP) m/z 214 (MH⁺)

EXAMPLES 66–79

Selected compounds listed in Table 12 were similarly prepared following the procedure outlined in Example 62 to 65, with appropriate selection and substitution of reagents, as listed in Table 13.

TABLE 12

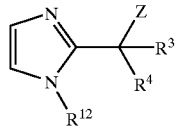

| Ex # | Z | R¹² | R³ | R⁴ |
|---|---|---|---|---|
| 66 | morpholin-1-yl | CH₃ | H | phenyl |
| 67 | —S-phenyl | CH₃ | H | phenyl |
| 68 | —NH-pyridin-2-yl | CH₃ | H | phenyl |
| 69 | —NH(CH₂OH₂OH) | CH₃ | H | phenyl |
| 70 | —S—CH₂CH₂NH₂ | CH₃ | H | phenyl |
| 71 | —NH-benzyl | CH₃ | H | phenyl |
| 72 | 4-methyl piperazin-1-yl | CH₃ | H | phenyl |
| 73 | imidazol-1-yl | CH₃ | H | phenyl |
| 74 | —NH-phenyl | CH₃ | H | ethyl |
| 75 | —NH-phenyl | CH₃ | H | —CH=CH₂CH₃ |
| 76 | piperidin-1-yl | CH₃ | H | —CH=CH₂CH₃ |
| 77 | morpholin-1-yl | CH₃ | H | —CH=CH₂CH₃ |
| 78 | morpholin-1-yl | CH₃ | H | ethyl |

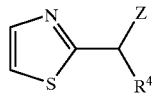

| Ex # | Z | R³ | R⁴ |
|---|---|---|---|
| 79 | piperidin-1-yl | H | phenyl |

TABLE 10

| | PREPARATION CONDITIONS | | | | |
|---|---|---|---|---|---|
| Ex # | reaction T (° C.) | reflux time (h) | yield (%) | mp (° C.) | mass spec (MH⁺) |
| 66 | reflux | 15 | 82 | oil | 258 |
| 67 | reflux | 6 | 86 | oil | 281 |
| 68 | reflux | 3 | 85 | oil | 265 |
| 69 | reflux | 20 | 65 | oil | 232 |
| 70 | reflux | 20 | 70 | oil | 249 |
| 71 | reflux | 24 | 76 | oil | 278 |
| 72 | reflux | 20 | 81 | oil | 271 |
| 73 | reflux | 20 | 75 | oil | 234 |
| 74 | reflux | 72 | 74 | oil | 216 |
| 75 | reflux | 4 | 88 | 122–123 | 228 |
| 76 | reflux | 4 | 60 | oil | 220 |
| 77 | reflux | 4 | 68 | oil | 222 |

TABLE 10-continued

| | PREPARATION CONDITIONS | | | | |
|---|---|---|---|---|---|
| Ex # | reaction T (° C.) | reflux time (h) | yield (%) | mp (° C.) | mass spec (MH⁺) |
| 78 | reflux | 72 | 40 | oil | 210 |
| 79 | reflux | 20 | 50 | oil | 259 |

While some the previous examples describe the purification of reaction products by flash chromatography, these reaction products can also be purified in a high-throughput mode using high-throughput reverse-phase or high-throughput normal phase HPLC instruments, thereby, increasing the efficiency of compounds library syntheses.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of synthesizing highly substituted azole compounds having the general formula (Ia):

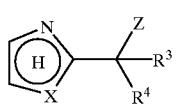

(Ia)

wherein

X is selected from the group consisting of NH, NR^A wherein R^A is hydrogen or —R wherein R is aralkyl;

wherein

is optionally substituted with one to three substituents independently selected from the group consisting of halogen, hydroxy, alkyl, halogenated alkyl; alkenyl, cycloalkyl, alkoxy, aryl, aralkyl, amino, mono- or di-substituted amino, cyano nitro, —COOR, —COR, —SO₂R and —CONR^B R^C; wherein the amine substituents are independently selected from alkyl, cycloalkyl, aryl or aralkyl; wherein the cyclalkyl or aryl may be further optionally substituted with one or more substituent is independently selected from halogen, hydroxy, alkyl, halogenated alkyl, alkoxy, amino, mono- or di-substituted amino, cyano or nitro;

Z is —OR^A wherein R^A is —CONR^C R^D:

R³ is selected from the group consisting of hydrogen, alkyl, aralkyl, cycloalkyl, and fluorinated alkyl; wherein the aralkyl may be optionally substituted with one or more substituents independently selected from halogen, hydroxy, alkyl, halogenated alkyl, alkoxy, amino, mono- or di-substituted amino, cyano or nitro;

R⁴ is selected from the group consisting of, alkyl, aryl, aralkyl, cycloalkyl, fluorinated alkyl, alkenyl, and alkynyl; wherein the alkyl, alkenyl, alkynyl, aryl or aralkyl may be optionally substituted with one or more substituents independently selected from halogen, hydroxy, alkyl, halogenated alkyl, alkoxy, aryl, amino, mono- or di-substituted amino, cyano or nitro;

R is selected from the group consisting of alkyl, aryl, aralkyl, cycloalkyl, and fluorinated alkyl; wherein the aryl or aralkyl may be optionally substituted with one or more substituents independently selected from halogen, hydroxy, alkyl, halogenated alkyl, alkoxy, amino, mono- or di-substituted amino, cyano or nitro;

$R^B$ is independently selected from the group consisting of hydrogen, —R, —COOR, —COR, —SO₂R, —SOR and —CONR$^C$R$^D$;

$R^C$ and $R^D$ are independently selected from the group consisting of hydrogen, alkyl, aryl, aralkyl, cycloaralkyl, and fluorinated alkyl; wherein the aryl or aralkyl may be optionally substituted with one or more substituents independently selected from halogen, hydroxy, alkyl, halogenated alkyl, alkoxy, amino, mono- or di-substituted amino, cyano or nitro;

which method comprises reacting a compound of formula (III)

(III)

with a compound of formula (IV)

(IV)

wherein A is selected from F, Cl, Br or —OC(O)-t-butyl, and wherein V is a sterically hindered group, in a non-protic solvent;

and then reacting with a compound of formula (V)

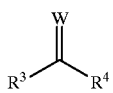
(V)

wherein W is O,
to form the corresponding compound of formula (Ic)

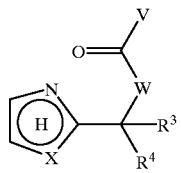
(Ic)

and reacting the compound of formula (Ic) with a compound of formula (VI)

Z—H (VI)

to yield the corresponding compound of formula (Ia).

2. The process of claim 1 wherein V is selected from the group consisting of t-butyl, O-t-butyl, O-isopropyl, O-adamantyl, adamantyl, N(alkyl)₂, N(aryl)₂, 2,6-dimethylphenyl, 2,6-disubstituted phenyl.

3. The process of claim 1 wherein the non-protic solvent is selected from the group consisting of acetonitrile, dioxane and THF.

4. The process of claim 1 wherein

is selected from the group consisting of imidazolyl, substituted imidazolyl (wherein the substituents on the imidazolyl group are one or more independently selected from halogen, alkyl, aryl, aralkyl, cycloalkyl, or alkoxycarbonyl, —C(O)N(alkyl)₂);

Z is —OC(O)N(alkyl)₂;

R³ is selected from the group consisting of hydrogen, alkyl, and trifluoromethyl;

and R⁴ is selected from the group consisting of alkyl, alkenyl, cycloalkyl, aryl, substituted aryl (where the aryl substituent is halogen, alkyl, alkoxy, nitro, amino, alkylamino or dialkylamino), and aralkyl.

5. The process of claim 4 wherein

is selected from the group consisting of 1-imidazolyl, 1-methyl-imidazolyl, 1-phenyl-imidazolyl, 1-benzyl-imidazolyl, 1-(di(i-propyl)aminocarbonyl)-imidazolyl, 1-methyl-5-chloro-imidazolyl, 1-methyl-4,5-dichloro-imidazolyl, and 1-methyl-5-methoxycarbonyl-imidazolyl;

Z is selected from the group consisting of —OC(O)N(methyl)₂, —OC(O)N(ethyl)₂, and —OC(O)N(i-propyl)₂;

R³ is selected from the group consisting of hydrogen, methyl, and trifluoromethyl;

and R⁴ is selected from the group consisting of methyl, ethyl, t-butyl, i-propyl, cyclohexyl, phenyl, 4-methoxyphenyl, 4-chlorophenyl, 4-nitrophenyl, benzyl, phenylethyl, —CH=CH₂, and —CH=CHCH₃.

* * * * *